United States Patent
Pellet et al.

(10) Patent No.: US 7,598,085 B2
(45) Date of Patent: Oct. 6, 2009

(54) TEST KIT FOR MEASURING THE LEVEL OF CARBOXYLATE ANION IN ENGINE COOLANT

(75) Inventors: Regis Joseph Pellet, Croton on Hudson, NY (US); Leonard S. Bartley, Jr., Newburgh, NY (US)

(73) Assignee: Chevron U.S.A. Inc., San Ramon, CA (US)

( * ) Notice: Subject to any disclaimer, the term of this patent is extended or adjusted under 35 U.S.C. 154(b) by 512 days.

(21) Appl. No.: 11/303,759

(22) Filed: Dec. 15, 2005

(65) Prior Publication Data

US 2007/0138434 A1    Jun. 21, 2007

(51) Int. Cl.
*G01N 31/00* (2006.01)

(52) U.S. Cl. .............................................. 436/5; 436/6
(58) Field of Classification Search ...................... 436/5, 436/6
See application file for complete search history.

(56) References Cited

U.S. PATENT DOCUMENTS

| | | | |
|---|---|---|---|
| 5,744,365 A | 4/1998 | Pellet et al. | |
| 5,952,233 A | 9/1999 | Pellet et al. | |
| 6,428,846 B2 * | 8/2002 | Kaupp et al. | 427/216 |
| 6,676,847 B2 * | 1/2004 | Turcotte et al. | 252/76 |
| 2005/0106748 A1 * | 5/2005 | Profitt et al. | 436/169 |

FOREIGN PATENT DOCUMENTS

JP    51023515 A * 2/1976

* cited by examiner

Primary Examiner—Lyle A Alexander
Assistant Examiner—Dennis M White
(74) Attorney, Agent, or Firm—Timothy J. Hadlock

(57) ABSTRACT

The invention includes, in one embodiment, a method for determining the presence or absence of a corrosion-inhibitory level of carboxylate anion in used engine coolant which includes: obtaining a known quantity of the engine coolant as a representative sample thereof, the sample containing a level of carboxylate anion to be determined; adding a fixed quantity of an aluminum containing color indicator to the sample, where the color of the aluminum color indicator is different from the original color of the sample, thereby changing the color of the sample to substantially the color of the aluminum color indicator, where at least a portion of the aluminum color indicator complexes with at least a portion of the carboxylate anion to form a colored insoluble aluminum-carboxylate complex, where the colored insoluble aluminum-carboxylate complex precipitates, and where the color of the sample remains substantially the color of the aluminum color indicator when the level of carboxylate anion therein is below an effective corrosion-inhibitory amount and where the color of the sample returns substantially to the original color of the sample when the level of carboxylate anion is at an effective corrosion-inhibitory amount; and observing the color of the sample.

7 Claims, 1 Drawing Sheet

TEST KIT FOR MEASURING THE LEVEL OF CARBOXYLATE ANION IN ENGINE COOLANT

FIELD OF THE INVENTION

Figure 1:
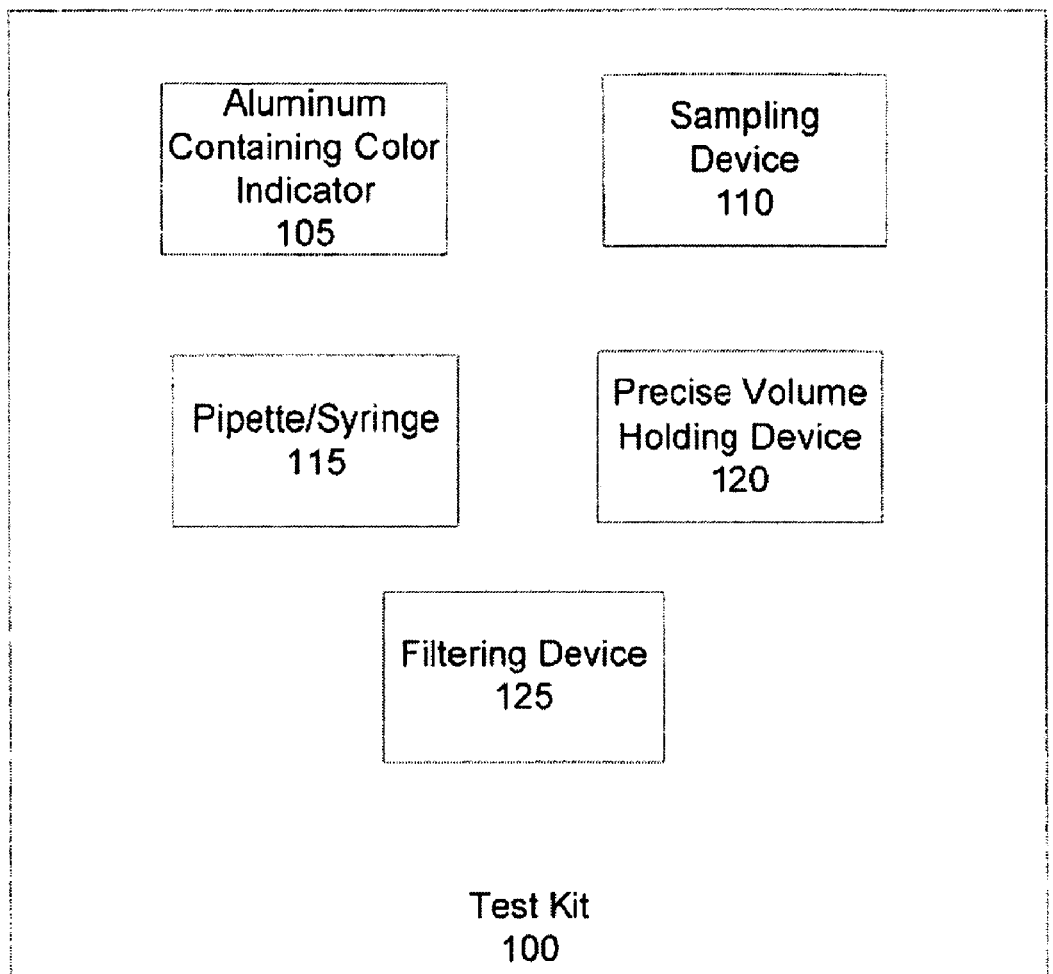

This invention relates to a method for measuring carboxylate anion present in used automotive and heavy duty engine coolants where it functions as a corrosion inhibitor and to a test kit for carrying out the method.

BACKGROUND OF THE INVENTION

Automotive engine cooling systems contain a variety of metals and metal alloys such as copper, solder, brass, steel, cast iron, aluminum and magnesium. The vulnerability of such metals to corrosive attack is high due to the presence of corrosive liquids and various ions as well as the high temperatures, pressures and flow rates characteristic of engine cooling systems. The presence of corrosion products within a cooling system can also interfere with heat transfer from the engine combustion chambers which may subsequently cause engine overheating and engine component failure.

Corrosion inhibitors are commonly added to engine coolants, e.g., silicates are added to provide aluminum protection, nitrites are added for cast iron protection and azoles may be added for copper and brass corrosion protection and to assist in the protection of iron and steel. All corrosion inhibitors employed in automotive antifreeze/coolant formulations are gradually depleted by use. The life expectancy of most coolants is about one to three years due to the progressive depletion of the corrosion inhibitor component(s). Carboxylic acids in the form of their salts have been incorporated into engine coolants to provide a greater degree of corrosion protection than other known types of corrosion inhibitors. Carboxylates are superior due to their slower depletion rates compared with other corrosion inhibitors. The life expectancy of carboxylate-containing coolants are typically five years or more.

For proper coolant maintenance, the engine operator should routinely monitor coolant levels to determine that the coolant is providing suitable boil and freeze point protection. To maintain adequate levels of corrosion inhibitor, it is also essential that the engine operator continually monitor corrosion inhibitor level as well as water content, coolant level, and visual appearance of the coolant.

In order that an engine coolant provide adequate corrosion protection, it is necessary that the coolant's corrosion inhibitors be present at a certain minimum level. When the concentration drops below this minimum, engine components may be damaged due to corrosion, so the inhibitors should be replenished as needed. Replacement of the entire coolant may be required when severe deterioration or contamination occurs. Inhibitor levels can often drop below the desired level when the engine coolant is inadvertently or intentionally topped off with either water or with another coolant product. Without appropriate tests, it is often difficult or impossible to determine that the required minimum corrosion inhibition is present. Of course a coolant can be sent to the appropriate laboratory for analysis to determine inhibitor level but this is costly and time consuming. In order that the engine operator can take timely corrective action, it is important that a quick determination can be made as to the level of protection afforded by the coolant.

There are field test available but typically they have limited applicability or are difficult to use. For example, nitrite test strips can be used to alert the user to low nitrite levels. Nitrite is required by some coolants in order to provide cast iron cylinder liner protection. These test strips have limited applicability in that they give no indication about protection of all other cooling system metals, such as aluminum, solder and copper. Carboxylates as well as phosphate, borate and tolyltriazole are inhibitors that provide protection for these metals. There are no reliable field tests for phosphate, borate and triazole inhibitors.

Some carboxylate-based coolants (also referred to as OAT coolants) provide a broad spectrum of corrosion protection for an array of metals including iron, steel, aluminum, solder and copper. There are field tests to determine alkyl carboxylate levels but these tests are difficult to apply, involving several steps and coolant manipulations. Because of the difficulties involved, the end user may be hesitant to perform the test and so may let his system go unmonitored. A more dangerous situation may develop if the field test is used incorrectly suggesting the wrong course of action.

Field tests for alkyl carboxylate-based coolants are described in U.S. Pat. Nos. 5,952,233 and 5,744,365. These patents describe a process where a predetermined amount of alkyl carboxylate-based coolant is treated with a predetermined quantity of aluminum cation solution. An aluminum carboxylate soap will precipitate from solution. The resulting mixture is then filtered and the filtrate is tested for the presence of aluminum using an Indicator solution under conditions that must be adjusted so that the indicator will react with aluminum cation. A problem with this method is that if interfering ions are present in the coolant, these ions must be removed by additional chemical treatment prior to testing for aluminum ion. Interfering ions are those ions which will also react with the indicator to give a color change and thus confuse interpretation of the aluminum analysis if they are not removed in advance. If the presence of aluminum is detected in the filtrate, then there was insufficient alkyl carboxylate in the initial coolant to provide adequate protection. Conversely, if aluminum is not detected in the filtrate, then there was sufficient carboxylate for adequate protection and the coolant passes.

A simplified summary of the process taught in U.S. Pat. Nos. 5,952,233 and 5,744,365 for carboxylate determination is depicted by the following reactions:

$$EHA + Al^{+3} \rightarrow Al(EHA)_2 \text{ soap} + \text{Excess } Al^{+3}$$

$$Al^{+3} + \text{color indicator} \rightarrow \text{Color change}$$

In this scheme EHA refers to the carboxylate component in a coolant sample, specifically, ethylhexanoate. In this method, the end user must first react coolant with aluminum and then test the resultant reaction mixture for excess aluminum. Another problem with this method, therefore, is that at best this is a two step process and in reality several steps including pH adjustment and filtration are required in order to develop the aluminum indicator colored complex. In addition, as previously mentioned, if there are any known interfering ions present in the coolant, they must be remove before the indicator can be added, thus adding yet another step. If unknown interfering ions are present, no corrective action can be taken and erroneous results are obtained.

In view of available tests, there is a need for a simple-to-use field test that overcomes the deficiencies of known methods for determining a coolant's ability to protect a broad array of cooling system metals.

SUMMARY OF THE INVENTION

This invention provides a simple, one-step test for alkyl carboxylate-based coolants. This invention describes an easy, one-step, colorimetric test that can be used by truckers, engine operators, and maintenance personnel in the field to determine if their OAT coolant has sufficient alkyl carboxylate inhibition to provide adequate protection for the engine's cooling system components.

The invention includes, in one embodiment, a method for determining the presence or absence of a corrosion-inhibitory level of carboxylate anion in used engine coolant which includes: obtaining a known quantity of the engine coolant as a representative sample thereof, the sample containing a level of carboxylate anion to be determined; adding a fixed quantity of an aluminum containing color indicator to the sample, where the color of the aluminum color indicator is different from the original color of the sample, thereby changing the color of the sample to substantially the color of the aluminum color indicator, where at least a portion of the aluminum color indicator complexes with at least a portion of the carboxylate anion to form a colored insoluble aluminum-carboxylate complex, where the colored insoluble aluminum-carboxylate complex precipitates, and where the color of the sample remains substantially the color of the aluminum color indicator when the level of carboxylate anion therein is below an effective corrosion-inhibitory amount and where the color of the sample returns substantially to the original color of the sample when the level of carboxylate anion is at an effective corrosion-inhibitory amount; and observing the color of the sample.

The invention includes, in another embodiment, a test kit for determining the presence or absence of a corrosion-inhibitory level of carboxylate anion in a representative sample of used engine coolant which includes an aluminum containing color indicator which forms an irreversibly colored insoluble aluminum-carboxylate with any alkyl carboxylate anion in the sample, and where after precipitation of the colored insoluble aluminum-carboxylate, the color of the sample remains substantially the color of the aluminum color indicator when there is insufficient carboxylate anion present to provide a predetermined level of corrosion inhibition.

These and other features and advantages of the present invention will be made more apparent through a consideration of the following detailed description of preferred embodiments of the invention.

BRIEF DECRIPTION OF THE DRAWINGS

FIG. 1 depicts in one embodiment the test kit of the invention.

DETAILED DESCRIPTION OF PREFERRED EMBODIMENTS

The corrosion inhibitors whose levels are determined in accordance with the method of this invention are the alkali metal or ammonium salts of carboxylic acids that form a water insoluble aluminum-carboxylate complex upon reaction with a source of aluminum cation. Examples of such alkali metal or ammonium salts are those of suberic acid, azelaic acid, undecanedioic acid, dodecanedioic acid, propionic acid, butyric acid, valeric acid, caproic acid, ethylhexanoic acid, octanoic acid, nonanoic acid, decanoic acid and undecanoic acid and their isomers, cyclohexane carboxylic acid, and the like. A preferred carboxylate corrosion inhibitor is an alkali metal ethylhexanoate, e.g., sodium ethylhexanoate, potassium ethylhexanoate, etc. Without in anyway limiting the scope of the invention, it is believed that alkyl carboxylate-based coolants provide metal corrosion protection by forming a metal carboxylate complex, i.e., soap, on the metal components surface where potential corrosion may be imminent. These soaps are insoluble and form a protective barrier at the site of imminent corrosion and nowhere else. It is believed that carboxylates can protect aluminum, iron and other metals in motor vehicle engines by this localized insoluble soap formation.

When a solution of metal cations is added to a carboxylate-based coolant, the metal-carboxylate soap or complex is observed to form as an insoluble precipitate in solution. If sufficient carboxylate is present, all metal cation will be removed from solution as the insoluble precipitate.

An Indicator solution is prepared by reacting a dye, e.g., Pyrocatechol Violet, with a metal cation, e.g, aluminum cation, in aqueous solution to form a soluble metal-dye complex, e.g., aluminum-dye complex. The indicator solution is prepared to contain a known concentration of the, e.g., aluminum-dye complex. For example, aluminum-dye indicator solutions can be prepared to contain 0.1-2.0 millimoles of aluminum per 100 g of indicator solutions, preferably 0.4 to 1.2 millimoles of aluminum per 100 g of solution.

A known quantity of used automotive or heavy duty engine coolant is withdrawn from the engine cooling system to provide a representative sample whose carboxylate anion content is to be determined. Generally, the amount of the coolant sample can vary from about 0.1 to about 100 g and preferably from about 1 to about 30 g. A fixed quantity of a source of an indicator solution, is then added to the sample. The precise quantity of indicator solution will depend upon the size of the coolant sample and the mole percent of carboxylate anion required for adequate corrosion protection. Routine testing can be carried out to provide stock solutions of suitable indicator solution concentrations for particular coolant formulations.

A predetermined quantity of this indicator solution is added to a predetermined quantity of an alkyl carboxylate anion containing based coolant. The carboxylate anion in the coolant is selected from the group consisting of the alkali metal of an aliphatic carboxylic acid. In a preferred embodiment, the carboxylate anion is ethylhexanoate anion. Ethylhexanoate-based coolants which are commercially available include DELO® Extended Life Coolant available from Chevron Corporation or TEXACO® Extended Life Coolant also available from Chevron Corporation.

When the indicator solution is added to the coolant at the predetermined levels, a reaction of the coolant's alkyl carboxylate with the aluminum-dye will form a colored insoluble aluminum-carboxylate complex which will precipitate and thus separate from the liquid phase. If sufficient alkyl carboxylate is present, all the aluminum dye will be removed and the resultant coolant indicator mixture will retain the color of the initial coolant, which is red in the case of the two coolant brands referenced above. If insufficient alkyl carboxylate is present, some of the aluminum dye (blue for aluminum plus, e.g., pyrocatechol violet) will remain in the coolant indicator mixture and the mixture will appear the color of the aluminum-dye indicator solution (blue where the dye is, e.g., pyrocatechol violet).

Thus if the liquid phase appears to be the color of the coolant, sufficient alkyl carboxylate is present and the coolant is deemed acceptable. If the liquid phase appears the color of the aluminum-dye complex, then insufficient alkyl carboxylate is present and the coolant is deemed unacceptable for adequate protection. It is important that the liquid phase be viewed to make the determination as the precipitated solid will always remain the color of the initial metal-dye complex. The indicator solution can be prepared using any metal ion that is known to irreversibly form an insoluble complex with the alkyl carboxylate, such as ethylhexanoate, to be tested. In one preferred embodiment the metal ion is an aluminum cation and is provided by an aluminum salt selected from the group consisting of aluminum chloride, aluminum sulfate, aluminum nitrate and their hydrates.

A dye is selected based on its known tendency to irreversibly complex with the selected cation. The dye is also selected to be a color different than that of the coolant color so that the absence/presence of the metal indicator complex can be detected based on color change. For a red-colored EHA-based coolant, such dyes include but are not limited to pyrocatechol violet, hematoxylin, Eriochrome Cyanine R, aurintricarboxylic acid, Pantachrome Blue Black R, and Alizarin S.

To summarize, a pre-measured amount of indicator is added to a measured amount of coolant and mixed; the color of the resulting solution (liquid) phase determines if the coolant is acceptable "as is" of if remedial action is needed. The present invention involves a simple one-step process that indicates coolant condition.

The current invention can be summarized as follows:

$Al^{+3}$ + Aluminum color indicator → Indicator Solution

Indicator Solution + EHA → Color Change

Again, EHA refers to ethylhexanoate. There are two unexpected advantages that accrue to the present invention that are not possible with known methods.

In the present invention, the aluminum-indicator complex can be made under controlled conditions with no interferences present. Moreover, the aluminum indicator complex can be supplied to the end user in a ready-to-use form. Thus, the first advantage of the present invention is that the many steps of the prior art are reduced to one step as far as the end user is concerned. A second advantage is that the possibility for interferences (both known and unknown) when forming the aluminum indicator complex is removed. In summary, the present invention is simpler and more accurate than the known methods.

It is further within the scope of the invention to provide a kit containing the apparatus and/or reagents necessary to carry out the foregoing test method in the field. A complete kit would contain all of the equipment and consumables for conducting at least one test procedure. Thus, such a kit would include a device for obtaining a test sample of coolant, e.g., a pipette or syringe for drawing coolant, at least one device for holding a precise volume of coolant liquid, e.g., a flask or column, a precise volume of indicator solution.

Optionally, the kit can contain a filtration device, e.g., a funnel and filter paper, to separate suspended particles from the coolant sample following formation of the insoluble aluminum-carboxylate complex. A partial test kit would include, at a minimum, the indicator solution.

ILLUSTRATIVE EMBODIMENTS

Specific illustrative embodiments of the present invention are as follows:

Illustrative Embodiment 1

A stock solution of pyro catechcol violet was prepared by dissolving 0.1 grams of pyro catechol violet in 100 grams of deionized water (this will be referred to as PCV solution). A supply of indicator solution was prepared by mixing 0.3 grams of aluminum nitrate nonahydrade, 3.8 grams of PCV solution and 95.9 grams of deionized water. The indicator solution contained 0.0008 moles of aluminum cation per 100 g of indicator solution. Pyro catechol violet is a dye that changes from orange to blue/violet in the presence of aqueous aluminum cation.

In order to demonstrate the effect of varying coolant carboxylate levels a series of test coolants were prepared. Test coolant solutions were prepared by mixing varying amounts of deionized water with Prediluted 50/50 TEXACO® Extended Life Coolant ("TELC"), a coolant containing about 1.6% ethylhexanoate (EHA), 50% ethylene glycol, and 50% water. A test coolant, designated 100% represents Prediluted 50/50 TELC to which no additional water was added. A test coolant designated 90% TELC represents TELC diluted by the addition of 10% deionized water (e.g. 9 grams of coolant plus 1 gram of deionized water.) A test coolant designated 80% TELC represents TELC diluted by the addition of 20% deionized water. In similar fashion, test coolants were prepared as 70% and 60% TELC. In this series, 100% TELC test coolant contains a full dose of the carboxylate, EHA. Specifically, this test coolant contains 1.6 wt % EHA or about 0.013 moles of ethylhexanoate for every 100 grams of coolant. A summary of test coolant EHA contents is provided in Table 1 below:

TABLE 1

Test Coolant EHA Concentration

| % Coolant | Moles EHA per 100 g |
|---|---|
| 100 | 0.0113 |
| 90 | 0.0101 |
| 80 | 0.0090 |
| 70 | 0.0079 |
| 60 | 0.0068 |
| 50 | 0.0056 |

In this illustrative embodiment, each test coolant was evaluated by mixing 0.3 grams of test coolant with 2.0 grams of indicator solution, mixing well and then allowing the resultant mixture to rest so that the resulting precipitate separated from the mixture. Again, the precipitate is the solid phase formed by the reaction of EHA with aluminum-PCV complex.

Tests conducted on the 60% and 70% coolants produce a liquid phase that is blue in color; this blue coloration indicates that there is still aluminum-PCV present in solution. In turn this indicates that there was insufficient EHA added to fully precipitate all of the aluminum-PCV indicator initially added to the coolant. In contrast, tests conducted on the 80, 90 and 100% coolants produce liquid phases that are tinted pink, retaining the red dye component of the starting coolant. All the blue aluminum-PCV has been removed from the solutions by the reaction with EHA in the test coolants. Thus there is sufficient EHA in the 80, 90 and 100% coolants to remove all of the aluminum ion (with its associated blue PCV dye) that was added in the indicator solution. The test coolant concentration at which this color change is observed can be varied by changing the ratio of indicator solution to coolant. For example, if the color transition were to occur at 30 to 40%, then half the amount of aluminum indicator solution could be added to the same amount of test coolant. In other words, to see a transition between 30 to 40%, it would be necessary to mix 0.15 grams of indicator solution with 2.0 grams of coolant to be tested.

The current transition from 70 to 80% coolant is appropriate for TELC since the TELC in this example provides adequate protection down to 80% dilution but would not provide adequate protection at 70% and lower dilutions. In this Illustrative Embodiment 80, 90 and 100% coolants would pass the test. The 70 and 60% coolants would fail.

Illustrative Embodiment 2

A second illustrative embodiment will demonstrate the accuracy of the present invention for evaluating carboxylate levels in coolant samples collected from an actual fleet of trucks that have been filled with TELC and have been contaminated or diluted with water or with other non-carboxylate coolants to a varying degree during actual use in the field.

Coolant samples were collected from each of thirty trucks operating in over-the-road service and each sample was analyzed by liquid chromatography (LC) to determine, accurately, the amount of ethylhexanoate present. EHA levels for each coolant are summarized in Table 2 below.

An indicator solutions was prepared by dissolving 0.6 grams of aluminum nitrate nonahydrate and 1.92 grams of 0.1% PCV stock solution in 89.8 grams of deionized water.

Each coolant was tested by mixing 0.3 grams of coolant with 0.9 grams of indicator solution; to this mixture an additional 0.1 grams of deionized water were added to aid separation of the precipitate from the solution phase. The components were mixed and the resulting mixture was allowed to separate into a solid and solution phase. This separation occurred within 60 seconds. The color of the solution phase is noted in the Table 2 below along with the EHA content as determined by LC. As in Illustrative Embodiment 1, for this system, blue tinted liquid phase indicates insufficient EHA to precipitate all of the aluminum-PCV complex. Pink solution phase indicates that there is more than sufficient EHA to remove all aluminum-PCV from the solution phase. As mentioned in Illustrative Embodiment 1 above all reaction mixtures contained a blue precipitate, which must separate from the mixture so that the solution-phase color can be determined.

TABLE 2

| Test Results | | |
|---|---|---|
| Coolant Sample No | % EHA by LC | Test Mixture Color |
| 1 | 0.18 | blue |
| 2 | 0.39 | blue |
| 3 | 0.73 | blue |
| 4 | 0.81 | blue |
| 5 | 1.02 | blue |
| 6 | 1.04 | pale blue |
| 7 | 1.13 | pale blue |
| 8 | 1.15 | pink |
| 9 | 1.32 | pale pink |
| 10 | 1.34 | pink |
| 11 | 1.34 | pale blue |
| 12 | 1.39 | pink |
| 13 | 1.39 | pink |
| 14 | 1.41 | pale pink |
| 15 | 1.44 | pink |
| 16 | 1.47 | pale pink |
| 17 | 1.48 | pink |
| 18 | 1.51 | pink |
| 19 | 1.54 | pink |
| 20 | 1.55 | pink |
| 21 | 1.59 | pale pink |
| 22 | 1.63 | pale pink |
| 23 | 1.72 | pink |
| 24 | 1.8 | pink |
| 25 | 1.82 | pink |
| 26 | 1.84 | pink |
| 27 | 1.88 | pink |
| 28 | 2.12 | pink |

TABLE 2-continued

| Test Results | | |
|---|---|---|
| Coolant Sample No | % EHA by LC | Test Mixture Color |
| 29 | 2.3 | pale blue |
| 30 | 2.36 | pink |

As with Illustrative Embodiment 1, Pre-diluted 50/50 TELC contains 1.62% ethylhexanoate (EHA). As can be seen from Table 2 above, EHA levels vary widely representing a range of coolant maintenance practices. For this Illustrative Embodiment, if we specify that coolants with more than 70% of their fresh EHA level are acceptable, then all coolants with 70% of 1.62% EHA, should be acceptable. Specifically, coolants with EHA contents greater or equal to 1.15% should pass or give a pink solution phase while all coolants with less than 1.15% EHA should fail or give a blue solutions phase.

Accordingly, test results in Table 2 indicate that all but two coolants gave the correct results. All coolants containing 1.15% or more EHA yield a test solution which is pink (with the exception of two samples). All coolants with less EHA yield a test solution which is blue. The two exceptions may be explained by experimental error arising from a failure to adequately separate the precipitate phase from the liquid portion of the mixture.

Other Implementations/Embodiments

Other embodiments of the present invention and its individual components and/or steps will become readily apparent to those skilled in the art from the foregoing detailed description. As will be realized, the invention is capable of other and different embodiments, and its several details are capable of modifications in various obvious respects, all without departing from the spirit and the scope of the present invention. Accordingly, the detailed description is to be regarded as illustrative in nature and not as restrictive. It is therefore not intended that the invention be limited except as indicated by the appended claims.

What is claimed is:

1. A method for determining the presence or absence of a corrosion-inhibitory level of carboxylate anion in used engine coolant which comprises:
    a. obtaining a known quantity of the engine coolant as a representative sample thereof, the sample containing a level of carboxylate anion to be determined;
    b. adding a fixed quantity of an aluminum containing color indicator to the sample, wherein the color of the aluminum color indicator is different from the original color of the sample, thereby changing the color of the sample to substantially the color of the aluminum color indicator, wherein at least a portion of the aluminum color indicator complexes with at least a portion of the carboxylate anion to form a colored insoluble aluminum-carboxylate complex, wherein the colored insoluble aluminum-carboxylate complex precipitates, and wherein the color of the sample remains substantially the color of the aluminum color indicator when the level of carboxylate anion therein is below an effective corrosion-inhibitory amount and wherein the color of the sample returns substantially to the original color of the sample when the level of carboxylate anion is at an effective corrosion-inhibitory amount; and c. observing the color of the sample.

2. The method of claim 1 wherein the carboxylate anion is selected from the group consisting of the alkali metal of an aliphatic carboxylic acid.

3. The method of claim 2 wherein the carboxylate anion is ethylhexanoate anion.

4. The method of claim 1 wherein the aluminum color indicator is made by reacting a dye with an aluminum cation to form an aluminum-dye complex.

5. The method of claim 4 wherein the aluminum cation is provided by an aluminum salt selected from the group consisting of aluminum chloride, aluminum sulfate, aluminum nitrate and their hydrates.

6. The method of claim 4 wherein the dye is selected from the group consisting of pyrocatechol violet, hematoxylin, Eriochrome Gyanine R, aurintricarboxylic acid, Pantachrome Blue Black R and Alizarin S.

7. The method of claim 6 wherein the dye comprises pyrocatechol violet.

* * * * *